United States Patent [19]
Rowland

[11] Patent Number: 5,727,541
[45] Date of Patent: Mar. 17, 1998

[54] ATOMIZATION OF LIQUIDS

[76] Inventor: Stephen James Rowland, 52 Broadlands Avenue, Sheffield S19 6RL, England

[21] Appl. No.: 686,115

[22] Filed: Jul. 24, 1996

[51] Int. Cl.[6] ................................................. A61M 11/00
[52] U.S. Cl. .............................. 128/200.14; 128/200.17; 128/200.21
[58] Field of Search ........................ 128/200.14, 200.17, 128/200.21, 203.12

[56] References Cited

U.S. PATENT DOCUMENTS

| | | | |
|---|---|---|---|
| Re. 33,717 | 10/1991 | Svoboda | 239/338 |
| 254,988 | 3/1882 | Lochmann | 128/200.17 |
| 3,229,450 | 1/1966 | Stern | 128/200.17 |
| 3,468,614 | 9/1969 | Nilsson | 239/223 |
| 3,812,853 | 5/1974 | Crain | 128/200.17 |
| 4,093,124 | 6/1978 | Morane et al. | 239/327 |
| 4,221,332 | 9/1980 | Bals | 239/223 |
| 5,054,477 | 10/1991 | Terada et al. | 128/220.14 |
| 5,203,506 | 4/1993 | Gross et al. | 239/224 |
| 5,226,605 | 7/1993 | Bazergui et al. | 239/223 |

Primary Examiner—Aaron J. Lewis
Attorney, Agent, or Firm—Trexler, Bushnell, Giangiorgi & Blackstone, Ltd.

[57] ABSTRACT

The invention relates to the atomization of liquids. There are many fields of application where a spray mist or jet of fine droplets is required and where control over droplet size is important. Of particular significance is the medical field and the nebulizing of a drug to be administered to a patient by the inhaled route, where the deposition of the drug and its efficacy is a direct function of the droplet size. The object of the invention is to improve the control over droplet size, an objective met by a method and a construction where liquid is centrifugally forced between the plates forming a rotor, secured together with a spacing to provide an annular orifice or held together in abutting relationship with an ability for pressurized fluid to pass between the plates, the rotation of the rotor causing the forcing of the liquid through the orifice or between the plates and such that the centrifugal force and the Bernoulli effect causes the liquid to issue in the form of droplets of a predetermined size.

11 Claims, 2 Drawing Sheets

ATOMIZATION OF LIQUIDS

This invention relates to the atomisation of liquids and is particularly concerned with medical nebulisers.

It is known to use atomised liquids in the medical field, for the administration of required drugs to, such as, the bronchial tree or the alveoli of the lungs of a patient. Here it is well-known to employ a drug in liquid soluble form, and for the drug to be nebulised and administered via the inhaled route. To facilitate this nebulisers already exist and broadly fall into two categories, the first where compressed air or other inhalable gas is used to drive the liquid through a small orifice to nebulise the liquid by a venturi effect, and the second where nebulising is effected by ultrasonic vibration. Nebulisers of the first category are relatively inefficient. The deposition of the drug at its required site and its efficacy is a direct function of the droplet size of the nebulised liquid, and with compressed-air-driven nebulisers it is virtually impossible for there to be any control over droplet size, the droplets are non-uniform with a wide range of sizes, and as a direct consequence only a small proportion of the drug is deposited at the intended site. Nebulisers of the second category rely on high frequency sound waves focussed on the surface of the liquid to be nebulised. The sound waves are created by the vibration of a piezo-electrical crystal. Here again control over droplet size is limited and with the same result that only a proportion of the drug administered is effectively deposited at the intended site.

With nebulisers of either category they are generally operated by either mains supply or by relatively substantial rechargeable batteries, and consequently in addition to having inefficient control over droplet sizes, with then but a proportion of the drug being effectively deposited at its required site, they additionally have the disadvantage of being bulky, heavy and relatively expensive.

In an attempt to overcome the problems mentioned above, it is known from, for example, French Patent No. 993441, to provide a rotor driven at a relatively high speed, the rotor having a feed passsage for fluid, and whereby fluid can be ejected from within the rotor by centrifugal force and form drops of fluid. However, the construction illustrated has relatively flexible plate members forming the rotor to allow compression of the plates together, and consequently, on rotation of the rotor, an unpredictable degree of flexing of the rotor plates occurs that varies the gap at the periphery of the plates and results in the formation of drops of fluid of different sizes.

It is the object of the present invention to provide a means of atomising liquids that seeks to improve on the prior art mentioned above and provide considerable control over droplet size.

According to the present invention, a medical nebuliser comprising a rotor formed by upper and lower plate members, a chamber for the rotor, a drive means for the rotor, and an air inlet to an air exit from the chamber, is characterised in that the lower plate member is of generally Y-shaped configuration with a vertical axis portion having a centrally positioned liquid feed pipe extending below the surface of liquid to be atomised, the lower plate member having a peripheral flange and the upper plate member having a co-operating peripheral flange, the plate members providing a passageway for liquid leading to the peripheral flanges, the facing surfaces of the peripheral flanges being so formed as to provide an orifice means for fluid for the issue of fluid from within the rotor and into the chamber, the orifice means being less than 10 m and being of a size determined in accordance with a selected speed for the rotor, to cause the issue of fluid from within the rotor as droplets of predetermined uniform size.

Preferably, the drive means for the rotor is a small battery-driven electric motor such as are already known and capable of running at very high rates of revolution. Further preferably, said electric motor and battery are contained in their own housing that may be attached to, or formed integral with, the drum housing, with a drive shaft from the motor extending to the drum.

The rotor being formed by plate members suitably secured together, and the inner surfaces of the plate members being so structured as to provide the passageways and the associated outlet orifices, the spacing between the plates determines the size of the orifices, and enables such considerable control over orifice size as to allow the provision of very small orifices of the order of less than 10 microns, thus allowing the production of droplets of exceedingly small and controlled size.

According to a further aspect of the invention, a medical nebuliser comprises a rotor formed by upper and lower plate members, a chamber for the rotor, a drive means for the rotor, and an air inlet extending to an air exit from the chamber, and is characterised in that at least the upper plate member has a recess to cooperate with the inner face of the lower plate to form a chamber, the chamber communicating with the interior of a funnel extending from the lower plate to below the surface of liquid to be atomised, the upper and lower plates being secured together with their inner faces at their rims in tight abutting relationship, the upper plate having a boss with a bore for attachment to the drive means for the rotor, the bore having an air bleed passage, and whereby with the rotor rotated fluid is permitted to be drawn up through the funnel into the chamber where it is pressurised to cause the pressure between the plates at the rims to be relaxed and to allow fluid to ease between the plates to emerge at the periphery in droplets of a size determined by the rate of rotation of the rotor.

The rotor plates may be secured together by a number of equi-spaced set screws. Equally, the plates can be held in firm abutting relationship and then spot welded at aruately spaced points by an appropriate, e.g. ultrasonic, welding technique.

It is preferred that the inner face of the funnel is at an angle to the axis of the funnel between 7° and 11° and more preferably, 9°.

The bore through the boss in the upper plate is preferably outwardly tapered to match a correspondingly tapered drive shaft on the drive means, the bore having drive ribs to engage corresponding drive recesses in the drive shaft of the drive means.

With such a rotor with an external diameter of 35 mm, and rotated at 25,000 rpm, the effect is to generate a 6 bar pressure of fluid in the chamber formed between the rotor plates, and as a result, fluid easing between the plates emerges at the periphery and forms droplets of the order 17 to 23 micron. The size of droplet can be varied by varying the speed of the rotor, the lower the rotor speed the greater the droplet size, and vice versa.

The outlet from the chamber is preferably formed with a mouthpiece of a shape suited to be placed within the mouth of a patient. Preferably, an inlet to the chamber is an opening strategically located in the chamber wall, and provided with a filter.

The chamber may additionally serve as a container for the liquid drug, with an appropriate means provided to transport the drug from within the chamber to the rotor. Such a construction has the advantage that if, and during use, there is the gathering of droplets on the wall of the chamber, they drain back to the position of the bulk of liquid for subsequent feeding to the rotor.

The supply of liquid to the rotor may be by way of a supply line located centrally of the rotor and extending to an appropriate source of liquid supply and there may be pump or other suitable means to cause the supply of liquid to the rotor. Conveniently, however, the air chamber may also serve as a sump to contain liquid, and the supply line extend from the rotor to liquid contained in the sump.

The medical nebuliser may have a mouthpiece secured to the outlet from the gas chamber, and a filter means provided at the inlet to the chamber, enabling a patient to inhale air drawn through the chamber, with droplets of nebulisable drug entrained in the air.

It is the careful selection of an orifice size to suit the liquid medication and the intended application site in the body, and/or the careful selection of a rotor diameter and its angular velocity of rotation that enables the production of uniform droplets of liquid of required small size.

Two embodiments of the invention suited to use as a medical nebuliser will now be described by way of example with reference to the accompanying drawings in which.

Figure 1:
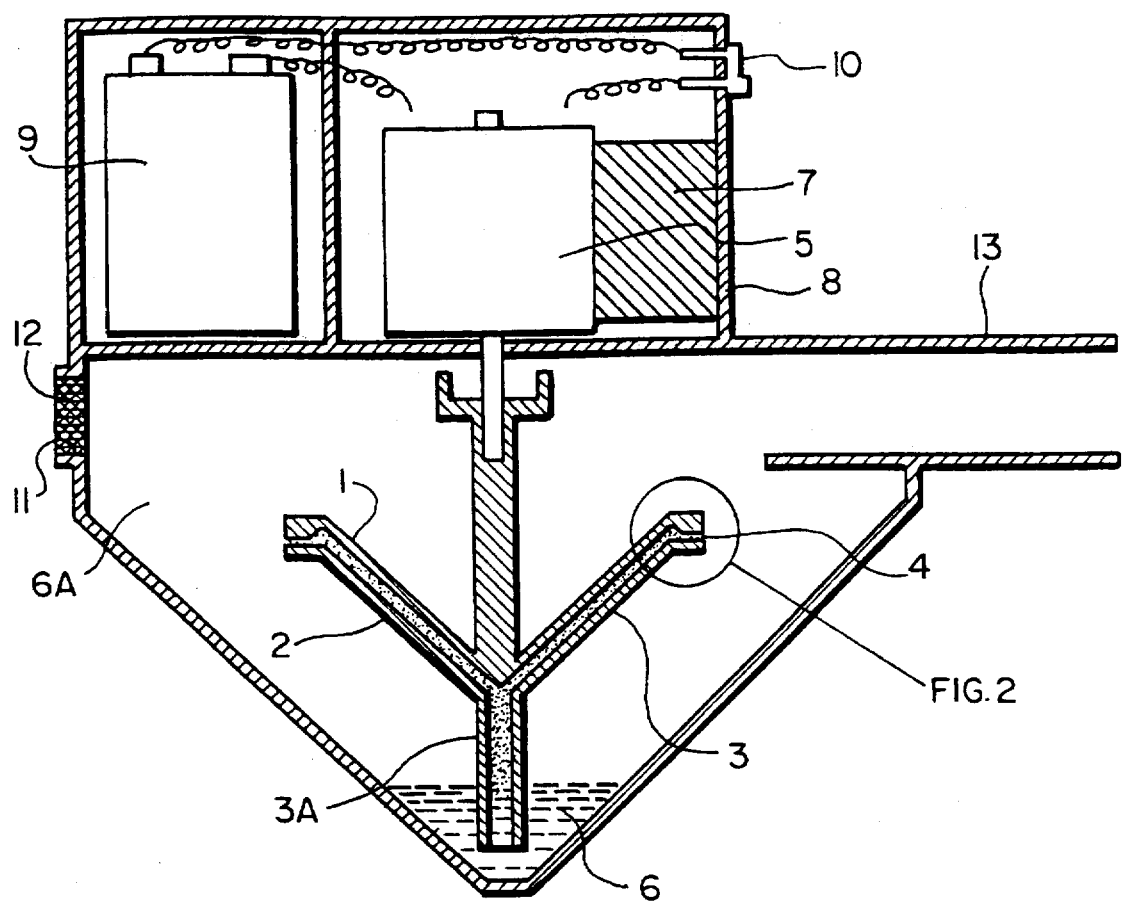
FIG. 1 shows a longitudinal section of a first embodiment of medical nebuliser in accordance with the invention.
Figure 2:
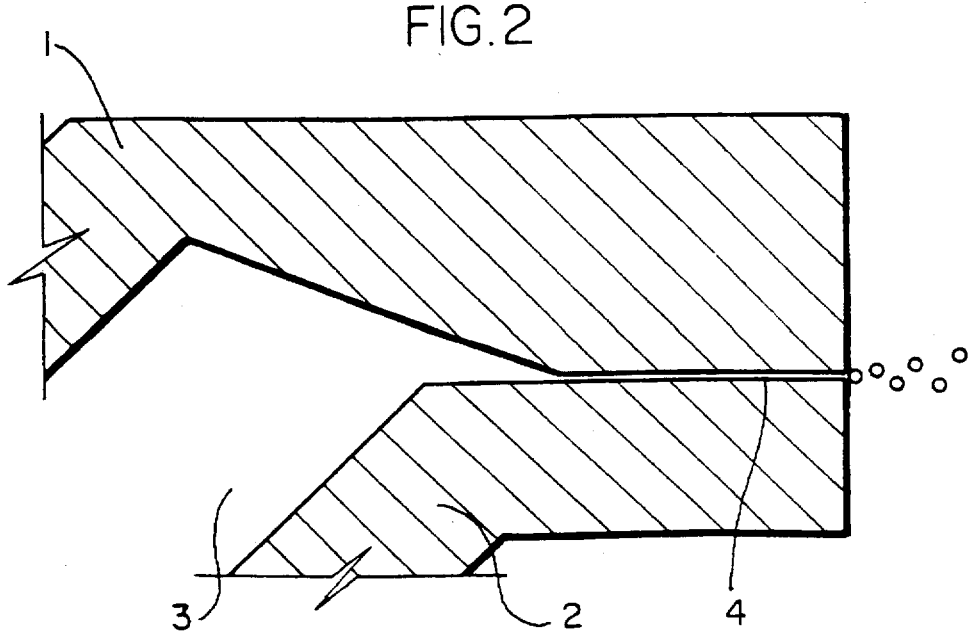
FIG. 2 is an enlarged section of the rim section of the rotor of FIG. 1.

In FIGS. 1 and 2 of the drawings a rotor is formed by two conical plates 1 and 2 suitably secured together to form a passageway 3 and a restricted orifice 4. The conical rotor so formed is driven by a direct current electric motor 5 but in many applications an induction motor may be employed to minimise vibration and starting torque. The plate 2 has a feed pipe 3A extending below the surface of a liquid to be atomised (nebulised) that is held in a sump 6 that also serves as an air chamber 6A to feed the rotor by capillary action or by way of a helical groove machined in the feed pipe. The motor is secured by a resilient mounting 7 to a housing 8 on the air chamber/sump to minimise vibration and optimise motor speed. The motor 5 is powered by a direct current source 9 and activated by a switch 10. A current limiting device may be required for smooth starting of the motor and to allow gradual attainment of operating speed. The atomised (nebulised) aerosol is contained in the sump 6 of the air chamber 6A. Air can be entrained through an inlet 11 which may be fitted as shown here with a filter 12 to prevent the ingress of particulate matter, and the aerosol inhaled by the patient through a mouthpiece 13 at the outlet from the air chamber.

In the example of a medical nebuliser shown, the orifice 4 is less than 10 microns and the required angular velocity of the motor 5 is of the order of 10,000 to 40,000 r.p.m. The sloping sides of the air chamber 6A ensures that any condensing or coalescing of the drug on it would be returned to the sump 6 and recirculated.

Figure 3:
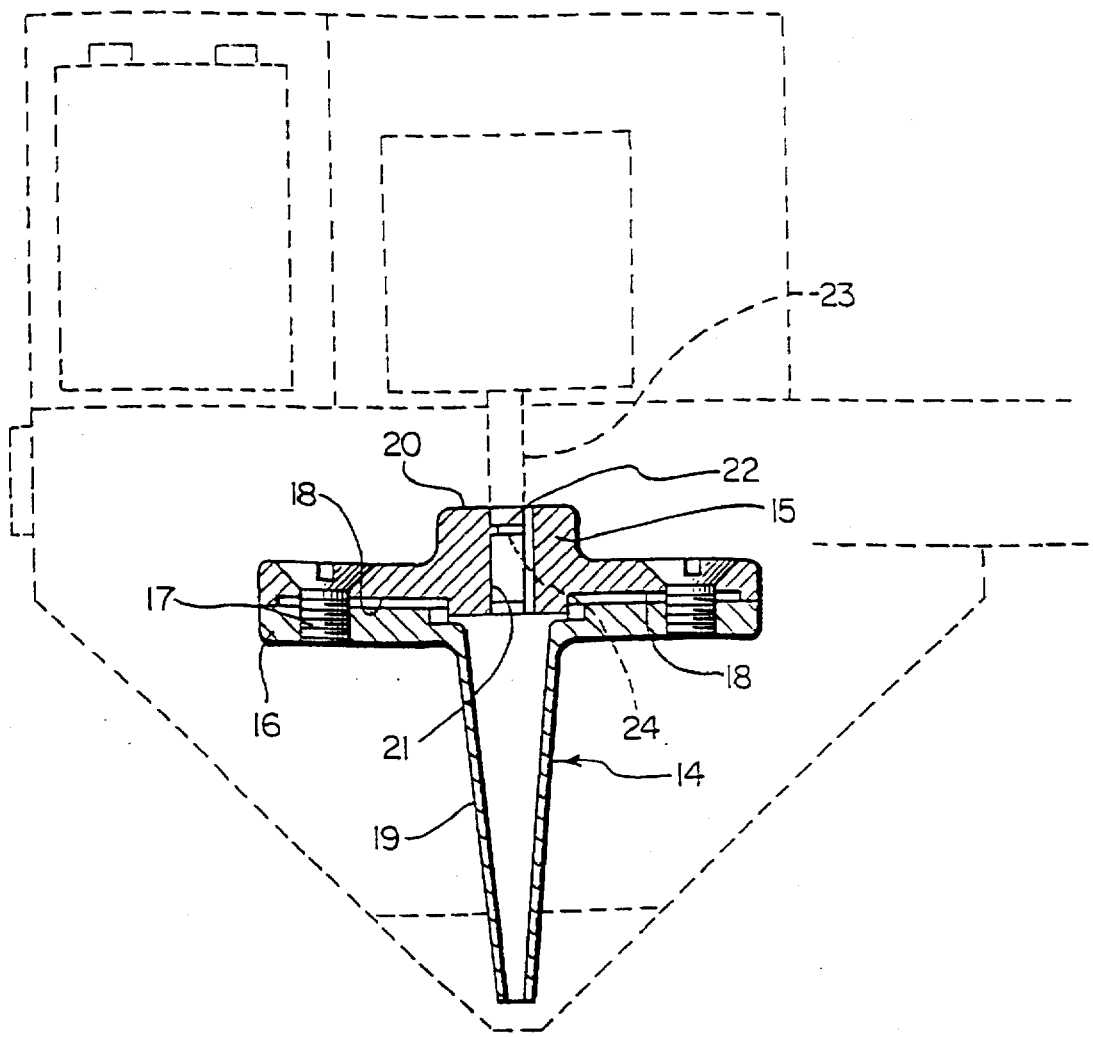
FIG. 3 is a sectional side elevation through an alternative construction of rotor for employment in a medical nebuliser such as is illustrated in FIG. 1.
Figure 4:
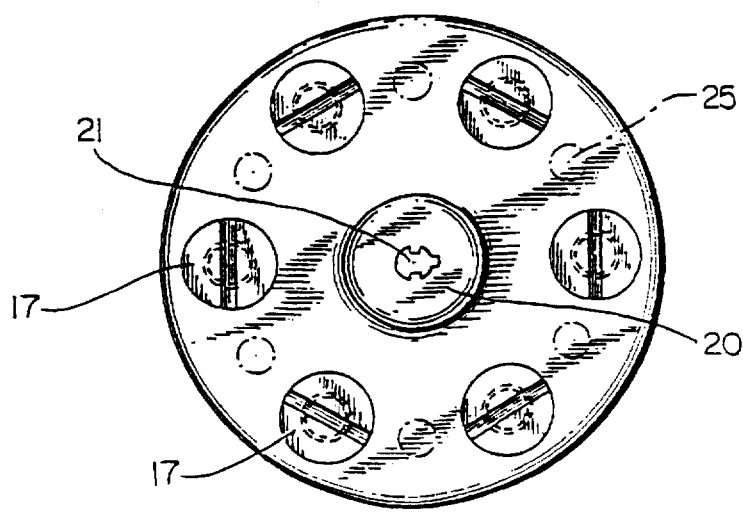
FIG. 4 is a plan view of the rotor of FIG. 3.

As is shown in FIGS. 3 and 4, an alternative construction of rotor 14 is formed by an upper plate 15 attached to a lower plate 16 by six equi-spaced set screws 17, and whereby the upper and lower plates can be tightly clamped together. The inner face of at least the upper plate 15 is recessed at 18, the recess co-operating with the inner face of the lower plate to form a chamber that communicates with the interior of a funnel 19, the inner surface of which is at 7° to 11° (preferably 9°) to the vertical axis of the funnel, and the funnel being open at its lower end such as to lie below the surface of liquid in the sump of the nebuliser. In the alternative, and as is generally indicated on FIG. 4, the set screws can be replaced by the welding together of the plates, the welding being spot welding at spaced locations as are indicated at 25.

Centrally of the upper plate 15 is a boss 20 having a shaped bore 21 which bore tapers inwardly of the boss, the wall of the bore 21 towards its upper end having a circumferential rib 22. A motor shaft 23 is correspondingly shaped and tapered, and has a circumferential recess 24 to receive the rib 22. Thus, the rotor can be pushed firmly on to the motor shaft to bring the circumferential rib 23 into engagement with the circumferential groove 24 and whereby the rotor is held firmly to the motor shaft with a non-slip drive between the shaft and the rotor. Additionally, the bore is provided with an air bleed passage over its full length.

Thus with fluid medicament in the sump of the nebuliser and with a rotor of a diameter of 35 mm rotated by the motor at approximately 25,000 rpm, the effect is for fluid to be drawn up the sloping surface of the funnel to fill the chamber formed in the rotor. Air in the funnel and air in the chamber between the plates is driven through the bleed passage whereby to ensure the absence of any resistance to fluid filling the chamber. Continued rotation of the rotor causes the fluid in the chamber to pressurise to approximately 6 bar, the effect of a 6 bar pressure between the rotor plates causing the pressure between the plates at their rims to be reduced to allow fluid to ease between the plates to emerge at the periphery, where it breaks free of the rotor in droplets of a guaranteed size between 17 and 23 micron. The actual size of the droplets can be varied by altering the rate of rotation of the rotor, the higher the speed the smaller the droplet size, and conversely, the lower the speed the greater the droplet size. As has been described in relation to FIGS. 1 and 2, the droplets of fluid can be entrained in an air flow through the nebuliser and out through a mouthpiece, any fluid not entrained in the air passing through the outlet draining down the wall of the sump of the nebuliser and back to the reservoir of fluid.

I claim:

1. A medical nebuliser comprising a rotor formed by upper and lower plate members, a chamber for the rotor, a drive means for the rotor, and an air inlet extending to an air exit from the chamber, is characterised in that at least the upper plate member has a recess to cooperate with the inner face of the lower plate to form a chamber, the chamber communicating with the interior of a funnel extending from the lower plate to below the surface of liquid to be atomised, the upper and lower plates having rims and being secured together with their inner faces at their rims in tight abutting relationship, the upper plate having a boss with a bore for attachment to the drive means for the rotor, the bore having and air bleed passage, means including rotation of the rotor for drawing fluid up through the funnel into the chamber, the rotation causing the plates at the rims to be relaxed and to allow fluid to flow, between the plates to emerge at the periphery in droplets of a size determined by the rate of rotation of the rotor.

2. A rotor as in claim 1, characterised in that the upper plate member (1) has a shape corresponding to that of the lower plate member (2).

3. A rotor as in claim 1 or claim 2, characterised in that the drive means for the rotor is a variable speed motor.

4. A medical nebuliser as in claim 1, characterized in that the drive means for the rotor is a motor located in a housing attached to or formed integral with the chamber.

5. A medical nebuliser as in any of claim 1, characterised in that an air filter is provided at the inlet to the chamber.

6. A medical nebuliser as in any of claim 1, characterised in that a mouthpiece is provided at the exit from the chamber.

7. A medical nebuliser as in any of claim 1, characterised in that the chamber (6A) is provided with a sump to hold fluid to be atomised.

8. A nebuliser as in claim 1, wherein the rotor plates are secured together by a number of equi-spaced set screws.

9. A nebuliser as in claim 1, wherein the plates are held in firm abutting relationship and then spot welded at arcuately spaced points by a welding technique.

10. A nebuliser as in claim 1, wherein an inner face of the funnel is at an angle to the axis of the funnel between 7° to 11° and more preferably, 9°.

11. A nebuliser as in claim 1 further including a drive shaft having a taper and at least one circumferential recess and wherein the bore of the boss of the upper plate is outwardly tapered corresponding to the taper of the drive shaft and has at least one drive rib, the drive rib and recess engaging each other.

* * * * *